(12) United States Patent
Paul et al.

(10) Patent No.: US 11,156,687 B2
(45) Date of Patent: Oct. 26, 2021

(54) MAGNETIC RESONANCE IMAGING

(71) Applicant: Siemens Healthcare GmbH, Erlangen (DE)

(72) Inventors: Dominik Paul, Bubenreuth (DE); Raphael Schwarz, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/807,350

(22) Filed: Mar. 3, 2020

(65) Prior Publication Data
US 2020/0300953 A1   Sep. 24, 2020

(30) Foreign Application Priority Data

Mar. 18, 2019   (EP) .................................... 19163417

(51) Int. Cl.
*G01R 33/56* (2006.01)
*G01R 33/54* (2006.01)
*G01R 33/567* (2006.01)

(52) U.S. Cl.
CPC ....... *G01R 33/5608* (2013.01); *G01R 33/543* (2013.01); *G01R 33/5673* (2013.01)

(58) Field of Classification Search
USPC ....................................................... 324/307
See application file for complete search history.

(56) References Cited

U.S. PATENT DOCUMENTS

2012/0121124 A1   5/2012   Bammer

OTHER PUBLICATIONS

European Search Report for European Application No. 19163417.9—1022dated Sep. 26, 2019.
M. Aksoy et al.: "Hybrid Prospective & Retrospective Head Motion Correction System to Mitigate Cross-Calibration Errors", Proceedings of the International Society for Magnetic Resonance in Medicine; ISMRM; 18th Scientific Meeting and Exhibition; Stockholm; Sweden; Apr. 17, 2010.
Orchard, Jeff, and Robert Staruch. "MRI reconstruction using real-time motion tracking: A simulation study." 2008 42nd Asilomar Conference on Signals, Systems and Computers. IEEE, 2008. pp. 1910-1914.
Zaitsev, Maxim, et al. "Magnetic resonance imaging of freely moving objects: prospective real-time motion correction using an external optical motion tracking system." Neuroimage 31.3 (2006): 1038-1050.

*Primary Examiner* — Rodney E Fuller
(74) *Attorney, Agent, or Firm* — Lempia Summerfield Katz LLC

(57) ABSTRACT

For improving image quality in MRI, a method for magnetic of an object is provided that includes obtaining MRI data during at least a first and a second acquisition step. Each acquisition step includes at least two data acquisition periods. A movement of the object is monitored by a camera system during the acquisition steps. Data obtained during the acquisition periods is adjusted based on the monitoring. Data obtained during a first reference period of the first acquisition step is compared to data obtained during a second reference period of the second acquisition step. The obtained or adjusted data is corrected based on a result of the comparison.

20 Claims, 3 Drawing Sheets

MAGNETIC RESONANCE IMAGING

CROSS REFERENCE TO RELATED APPLICATIONS

This patent application claims priority from European Patent Application no. 19163417.9 filed on Mar. 18, 2019, which is hereby incorporated in its entirety.

FIELD

Embodiments include a method for magnetic resonance imaging (MRI) of an object. MRI data is obtained during at least a first and a second acquisition step.

BACKGROUND

For several MRI applications, a sufficient signal-to-noise ratio, SNR, is required. This may be obtained by repeating MRI measurements and calculating respective averages. One example is the generation of synthetic contrast images, where, for example, a multi-repetition sequence with multi delay times may be used.

However, such approaches may suffer from the fact that a quality of the final images is very sensitive to motions of an object to be imaged between individual acquisition steps or repetitions and, if applicable, also between the different delay times. This may lead to motion artifacts in the final image.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide for MRI with at least two data acquisition steps, allowing for an improved image quality.

Embodiments monitor the object during each data acquisition step by a camera system and compensate the movement by a respective adjustment. In addition, the adjusted MRI data sets from different data acquisition steps are compared to each other and an additional correction of the MRI data is performed thereupon. Corrections of MRI data within and between acquisition steps are therefore separated.

According to an embodiment, a method for magnetic resonance imaging, MRI, of an object is provided. MRI data is obtained during at least a first and a second acquisition step, for example, data acquisition step. Each acquisition step includes at least two data acquisition periods. The MRI data are acquired during the data acquisition periods, for example exclusively during the data acquisition periods. A movement of the object is monitored by a camera system during the first and the second acquisition step. MRI data obtained during the acquisition periods is adjusted based on the monitoring. MRI data obtained during a first reference period of the at least two acquisition periods of the first acquisition step is compared to MRI data obtained during a second reference period of the at least two acquisition periods of the second acquisition step by a processing unit. For each of the at least two acquisition periods of the second acquisition step, the obtained or adjusted data is corrected based on a result of the comparison by the processing unit.

MRI data may for example correspond to signal data in position or momentum space from which a final MRI image may be deduced. In the following, "data" may refer to MRI data, unless otherwise stated.

The monitoring of the movement during the first and the second acquisition step may include a monitoring of the movement during the respective acquisition periods of the first and the second acquisition step, for example during all of the acquisition periods, and during periods between subsequent acquisition periods of a given acquisition step, if applicable.

The adjustment of the data based on the monitoring includes for example an adjustment depending on a result of the monitoring, for example depending on a movement detected by the camera system by the monitoring.

Individual acquisition periods of a given acquisition step may for example be separated by a predefined gap period. For example, the gap period may be identical for pairs of subsequent acquisition periods of a given acquisition step. Alternatively, all or some of the acquisition periods of a given acquisition step may overlap or follow each other without a gap period.

From a timewise perspective, the at least two data acquisition periods of the first step follow each other one after another. Afterwards, the at least two data acquisition periods of the second acquisition step follow one after another.

One or more additional acquisition steps may follow after the first and the second acquisition step and/or may lie before the first and the second acquisition step, each including at least two respective data acquisition periods.

The first reference period may for example correspond to an initial acquisition period of the first acquisition step. The second reference period may for example correspond to an initial acquisition period of the second acquisition step. Here, "initial" may refer to an order in time.

The correction of the obtained or adjusted data based on the result of the comparison may for example include a correction of the adjusted data, if the respective data of the corresponding acquisition period has been adjusted based on the monitoring, and a correction of the obtained data otherwise.

According to an embodiment, a monitoring of object movements or respective images taken by the camera system is combined with an MRI data comparison.

According to an embodiment, a movement of the object between subsequent acquisition periods is compensated by the monitoring by the camera system and a movement of the object between subsequent steps of the acquisition steps is compensated by the correction of the obtained or adjusted data.

Embodiments do not rely barely on a continuous monitoring by the camera system over several or all acquisition steps. For example, cumulative errors of the camera-based monitoring, for example due to possible imperfections of the adjustment based on the monitoring or of the camera-based monitoring itself, may be avoided by using the MRI data comparison to correct for movements between the individual acquisition steps. In some implementations, using the monitoring by the camera system is not necessary for movements of the object between subsequent acquisition steps.

The imperfection of the camera-based monitoring may for example origin from the fact that a movement of a marker or marker structure monitored by the camera system does not necessarily correspond to a movement of the presently imaged layer of the object exactly, since the object to be imaged is not necessarily a rigid body. Due to the combination of camera-based monitoring and the MRI data comparison, corresponding errors may be minimized.

Embodiments do not rely only on the comparison of MRI data of different acquisition steps but combines the comparisons with the camera-based monitoring. Therefore, at least in part, a real time or online data adjustment may be achieved. For example, a computation time needed for potential MRI data corrections within one acquisition step does not put restrictions on any gap periods between subsequent acquisition periods of a given acquisition step. Furthermore, a total computational effort for MRI data comparison and correction is reduced by the combination.

Consequently, embodiments allow for an improved motion compensation for MRI imaging, resulting in less motion artifacts in the final image.

The separation of monitoring within a given acquisition step from MRI data comparison between subsequent acquisition steps may be beneficial to reduce effects of distortion correction effects during scanning of the different repetitions or acquisition steps.

In an embodiment of the method, the adjustment of the data obtained during acquisition periods based on the monitoring is performed individually for each of the acquisition steps and for example the monitoring for different acquisition steps is performed independent of each other.

In an embodiment, the two or more acquisition periods of the first or the second acquisition step, respectively, correspond to respective repetitions of MRI measurements, for example equivalent MRI measurements.

In an embodiment, the first and the second acquisition step, and if applicable also the additional acquisition steps, correspond to different delay times or delay periods, for example after a magnetic preparation pulse applied to a specific layer of the object to be imaged.

In an embodiment, the MRI is performed according to a multi-delay and multi-echo data acquisition technique, MDME. The various delays correspond to the acquisition steps according to embodiments and the various echoes correspond to the individual data acquisition periods.

In an embodiment, the method includes establishing a magnetic resonance, MR, image of the object based on the corrected data, for example by the processing unit.

In an embodiment, the establishing of the MR image includes calculating respective average data for each of the acquisition steps by averaging the corrected data of all acquisition periods of the given acquisition step, for example by the processing unit.

In an embodiment, the establishing of the MR image includes establishing a synthetic contrast map, for example a T1-map, a T2-map and/or a flair-map, for example by the processing unit.

In an embodiment, the magnetic preparation pulse corresponds to a 120° pulse.

In an embodiment, for the adjustment of the data obtained during the acquisition periods based on the monitoring, respective data sets of each of the acquisition periods of the first and the second acquisition step are adjusted depending on a result of the monitoring, for example depending on a result of the monitoring of the respective acquisition period, for example by the processing unit.

For example, the adjustment depending on the result of the monitoring may include an adjustment, if a movement of the object is determined by the monitoring, and no adjustment otherwise.

In an embodiment, each of the data sets is adjusted at least once, for example twice or three times, during the respective acquisition period, depending on the result of the monitoring, for example by the processing unit.

The more often the adjustment is performed based on the monitoring, the better is the respective motion compensation.

For example, also data sets corresponding to the first or the second reference period may be adjusted. For example, the monitoring may for example detect also a movement of the object during the first or the second reference period. Therefore, the data set of the reference periods may be adjusted for example with respect to earlier states of the object or positions of the object within the reference period.

In an embodiment, for the adjustment of the data obtained during the acquisition periods based on the monitoring, images are taken by the camera system during different acquisition periods of the first acquisition step are compared to each other. The adjustment of the data obtained during the acquisition periods is carried out depending on the result of the comparison of the images, for example by the processing unit.

One of the different periods for which the images are taken by the camera system and compared to each other remains for example the same for all acquisition periods of a given acquisition step. It may for example correspond to the first reference period or to a further first reference period.

For example, the camera system takes images during all acquisition periods of each of the first and the second acquisition step, and the comparison and adjustment is performed as described for all of the acquisition periods.

In an embodiment, for the monitoring of the movement of the object, a movement of one or more markers attached to the object is monitored by the camera system.

The one or more markers may for example be attached to a nose or another body part of a person representing the object.

The one or more markers may for example include a two-dimensional or three-dimensional object of a defined shape or color or another property detectable by the camera system.

For the monitoring of the movement of the markers, positions of the markers in different acquisition periods of a given acquisition step are compared to each other and the adjustment is for example performed depending on a deviation of the positions of the markers.

By using the markers to monitor the movement of the object, a reliable recognition of the movement may be achieved. For example, due to the markers being attached to the object, a movement of the marker may be assumed to approximately reflect a corresponding movement of the object.

In an embodiment, the camera system includes at least two cameras having different positions with respect to at least one of the one or more markers.

By using more than one camera, for example four cameras, the position or location of the markers may be detected more reliably, for example a movement of the markers may be detected, independent of a direction of the movement.

In an embodiment, for the adjustment of the data obtained during the acquisition period based on the monitoring, at least one image taken by camera system during the first reference period is compared to at least one image taken by the camera system during a further acquisition period of the second acquisition step. The adjustment of the data obtained during the acquisition periods is carried out depending on a result of the comparison of the images, for example by the processing unit.

In such implementations, the camera-based monitoring is not only performed within acquisition steps, but also continuously over two or more subsequent acquisition steps and therefore with respect to movements of the object between subsequent acquisition steps.

For example, such implementations allow the MRI data comparison of different acquisition steps to be supported by a fully camera-based adjustment of all acquisition steps and periods, for example with respect to the first reference period.

Thus, a redundancy with respect to the MRI data comparison is provided and a higher accuracy of the artifact compensation may be achieved.

In an embodiment, a mapping rule is established, for example by the processing unit, depending on the result of the comparison of the data obtained during the first reference period to the data obtained during the second reference period. For each of the at least two acquisition periods of the second step, the obtained or adjusted data are corrected based on the mapping rule, for example by the processing unit.

For example, the mapping rule is established such that it maps the data of the first reference period to the data of the second reference period. The correction of the obtained or adjusted data is performed by applying an inverse of the mapping rule to the obtained or adjusted data resulting in the corrected data.

For example, for comparing the data obtained during the first and the second reference period, a pixel-wise comparison of all relevant pixels of MRI sub-images corresponding during the first and the second reference period is performed.

This technique may also be denoted as registration of the second to the first reference period. The correction of the data is then performed depending on the registration.

The approach based on the registration and the mapping rule may lead to very exact correction of the MRI data and improved compensation of movement artifacts.

In an embodiment, the mapping rule corresponds to a Euclidian transformation or rigid transformation.

In an embodiment, the establishing of the mapping rule and the correction based on the mapping rule is performed after the second acquisition step, for example after all acquisition steps of the at least two acquisition steps.

The Euclidian transformation, that is given by a geometric transformation persevering the Euclidian distance between every pair of points and may include rotations, translations, reflections, or combinations thereof, may for example be applied by a matrix operation.

In a embodiment, the data obtained during the acquisition periods of the first and the second acquisition step correspond to a layer of the object. If a gap period exists between successive acquisition periods data for a further layer of the object may be obtained during the gap periods.

In such implementations, the gap period may correspond to a time period that may have to be awaited and may be used in an efficient way. For example, the data for the further layer of the object may be obtained according to a method according to embodiments as well.

Overall, when imaging of all layers, less time may be consumed. This may be relevant for MDME techniques, where several repetitions have to be made.

In an embodiment, prior to or at the beginning of each of the acquisition periods of the first or the second acquisition step, an excitation pulse is applied to the object.

The excitation pulse includes for example a high frequency pulse for flipping nuclear spins in a respective layer of the object by the flip angle or Ernst angle. The flip angle may for example be 90°.

In an embodiment, each acquisition period corresponds to a single echo signal following a corresponding excitation pulse.

In an embodiment, exactly one excitation pulse is applied to the object for two or more subsequent acquisition periods of the first or the second acquisition step. For example, the excitation pulse is applied prior to or at the beginning of the first of the two or more subsequent acquisition periods. Then, there is no further excitation pulse until the two or more subsequent acquisition periods are over.

In other words, two or more echoes are acquired for each excitation pulse. For example, the two or more echo signals may correspond to two or more different echo times.

According to an embodiment, a system for magnetic resonance imaging, MRI, of an object is provided. The system includes an MRI scanner and a processing unit configured to control the MRI scanner to obtain MRI data during at least a first and a second acquisition step. Each acquisition step includes at least two data acquisition periods. The system for MRI further includes a camera system. The processing unit is configured to control the camera system to monitor a movement of the object during the first and the second acquisition step. The processing unit is also configured to adjust MRI data obtained during the acquisition periods based on the monitoring. The processing unit is further configured to compare MRI data obtained during a first reference period of the at least two acquisition periods of the first acquisition step to MRI data obtained during a second reference period of the at least two acquisition periods of the second acquisition step. Furthermore, the processing unit is configured too, for each of the at least two acquisition periods of the second step, correct the obtained or adjusted MRI data based on a result of the comparison.

Further implementations of the system for MRI follow readily from the various implementations and embodiments of the method according to an embodiment and vice versa. For example, the system for MRI is configured to perform a method.

According to a further embodiment, a computer program including instructions is provided. The instructions, when executed by a system for MRI, for example by the processing unit of the system for MRI, cause the system for MRI, for example the camera system, and the MRI scanner and the processing unit, to execute the steps of a method according to an embodiment.

According to an embodiment, a computer-readable storage medium, for example a non-transitory and/or tangible computer-readable storage medium, storing a computer program according to an embodiment is provided.

Several implementations of a system for MRI contain the computer-readable storage medium according to an embodiment, for example the processing unit or a computer of the system for MRI.

DETAILED DESCRIPTION

Figure 1:
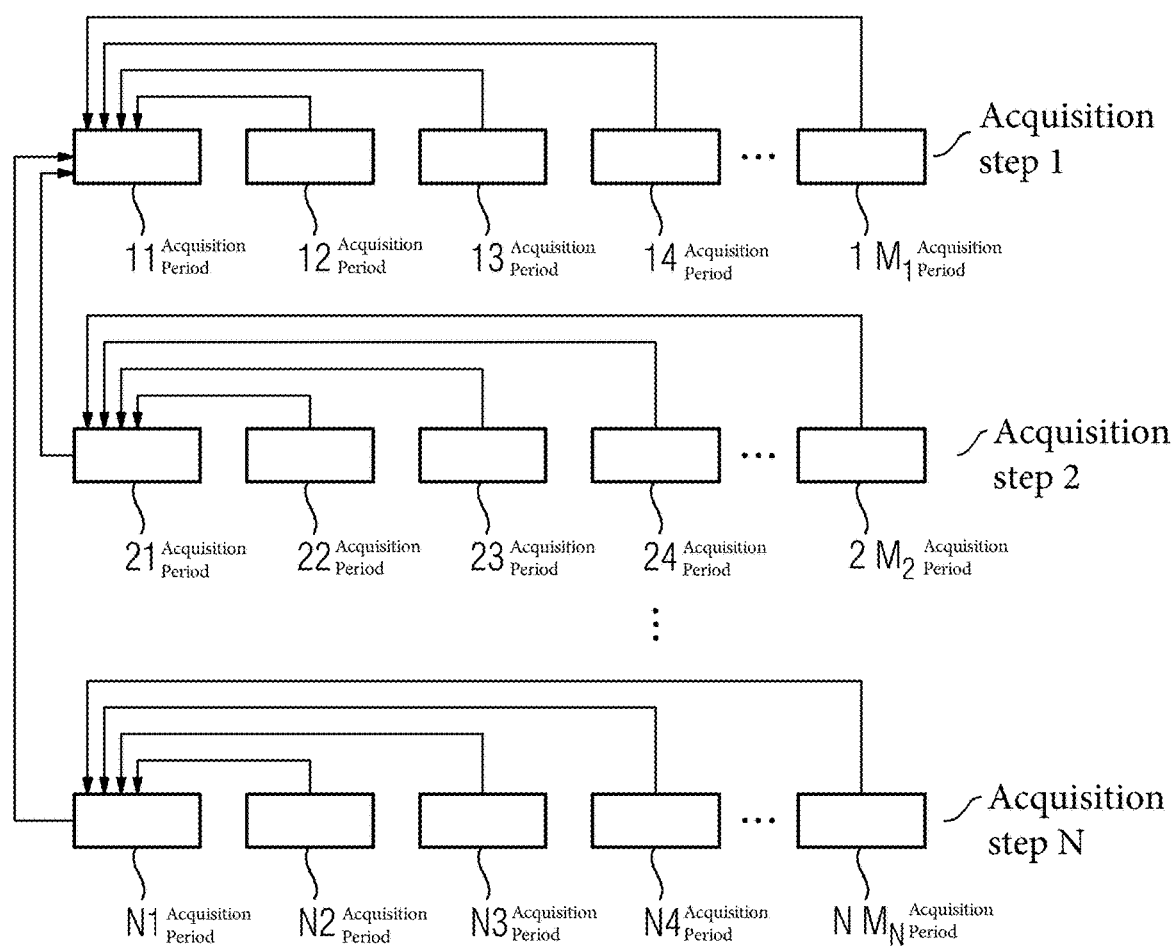
FIG. 1 depicts a schematic representation of a method according to an embodiment.

In FIG. 1, a schematic representation of a method according to an embodiment is shown.

The example of FIG. 1 may correspond to a multi-repetition sequence with multi delay times, also known as MDME. A first delay is denoted by 1, a second delay is denoted by 2 and an N-th delay is denoted by N. The different delays are also denoted as acquisition steps. Each acquisition step 1, 2, N includes a plurality of repetitions, that are also denoted as acquisition periods.

The first acquisition step 1 includes subsequent acquisition periods 11, 12, 13, 14, $1M_1$. Therein, $M_1$ denotes the total number of acquisition periods of the acquisition step 1. The second acquisition step 2 includes for example subsequent acquisition periods 21, 22, 23, 24, $2M_2$. Therein, $M_2$ denotes the total number of acquisition periods of acquisition step 2. For example, $M_1$ may be equal to $M_2$.

According to an embodiment, at least two acquisition steps 1, 2 are given. All further acquisition steps, for example the N-th acquisition step N are optional. In the shown example, the N-th acquisition step N includes subsequent acquisition periods N1, N2, N3, N4, $NM_N$. Therein, $M_N$ denotes the total number of acquisition periods of the acquisition step N. For example, $M_N$ may be equal to $M_1$ and/or $M_2$.

According to an embodiment, MRI data are obtained during each of the acquisition steps 1, 2, N, for example for each of the acquisition periods 11, . . . , $NM_N$.

During the acquisition periods 11, . . . , $1M_1$ of the first acquisition step 1, a camera system monitors a movement of an object to be investigated by the MRI. For example, at least once during each of the acquisition periods 12, 13, 14, $1M_1$, an image of the object is taken by the camera system and compared to an image taken by the camera system during a first reference period of the first acquisition step 1. The first reference period may for example be given by the initial acquisition period 11 of the acquisition step 1. The camera system may take images of the object more frequently, for example at least twice during each of the acquisition periods 12, 13, 14, $1M_1$ and at least once during the first reference period 11. All taken images are for example compared to an initially taken image during the first reference period 11.

A processing unit may compare the images taken by the camera system to the initial image taken during the first reference period 11. From a deviation of the images, data acquired or obtained during the respective acquisition periods 11, . . . $1M_1$ is adjusted. A motion of the object during the first acquisition step 1 may be compensated.

An analog data adjustment with respect to the camera-based monitoring during acquisition step 1 may also be performed during each of the subsequent acquisition steps 2, N.

For example, the adjustment of the data based on the comparison of the images taken by the camera system may be performed in real time or online during the respective acquisition steps 1, 2, N and/or during the respective acquisition periods 11, . . . , $NM_N$.

After the second acquisition step 2 is finished, for example after all acquisition steps 1, 2, N are finished, the data of the second acquisition step 2 and if applicable, of all of the acquisition steps following the second acquisition step 2, for example acquisition step N, are corrected based on a registration approach.

A second reference period 21 of the second acquisition step 2 is defined and is for example given by an initial acquisition period 21 of acquisition step 2. Data obtained during the second reference period 21 that may or may not be adjusted based on the camera-based monitoring, is compared to the data obtained or adjusted during the first reference period 11. Depending on the comparison, for example depending on deviations between the obtained or adjusted data corresponding to the reference periods 11, 21, a mapping rule is established according to which the data of the first reference period 11 is mapped to the data of the second reference period 21.

Then, the data of all acquisition periods 21, . . . , $2M_2$, of the second acquisition step 2 are corrected based on the mapping rule. For example, corrected versions of the data corresponding to the acquisition period 21, . . . , $2M_2$, may be obtained by applying an inverse of the mapping rule to the correspondingly obtained or adjusted data of the acquisition periods 21, . . . , $2M_2$.

The same registration or correction approach may be used for any of the following acquisition steps, for example the acquisition step N.

In the described way, a camera-based monitoring and a corresponding adjustment of the data is combined with a registration-based correction of MRI data of different acquisition steps.

The camera-based monitoring may be extended to a fully camera-based approach over several or all acquisition steps 1, 2, N. This fully camera-based approach is combined with the registration-based correction approach for different acquisition steps.

Figure 2:
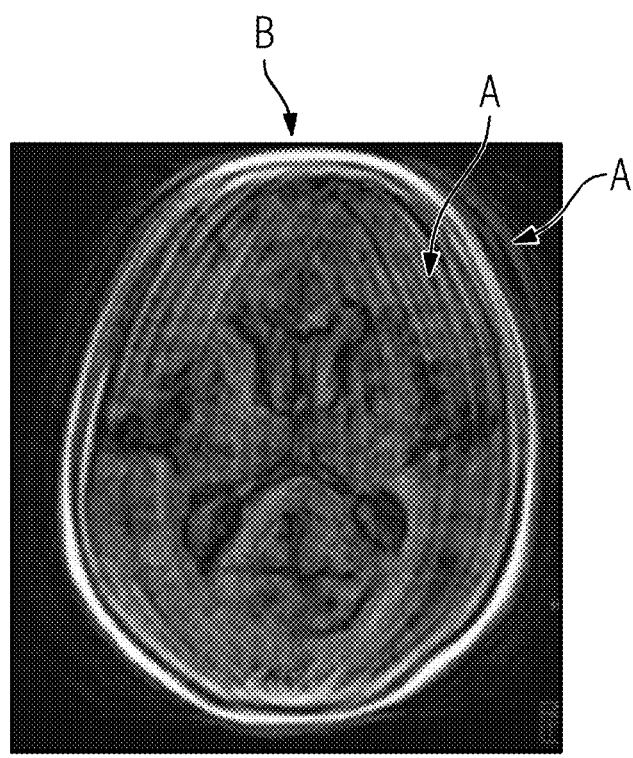
FIG. 2 depicts an example of an MR image according to an embodiment.

In FIG. 2, an MRI image B of a brain, for example a synthetic contrast image, taken by a conventional method for MRI is depicted. A movement of the brain during data acquisition has led to significant motion artifacts A in the final image.

Figure 3:
FIG. 3 depicts an example of an MR image acquired by a method according to an embodiment.

FIG. 3 depicts another MRI image of a brain as in FIG. 2, for example a synthetic contrast image, obtained by a method according to an embodiment. The motion artifacts are not present in this case or are at least significantly diminished.

Figure 4:
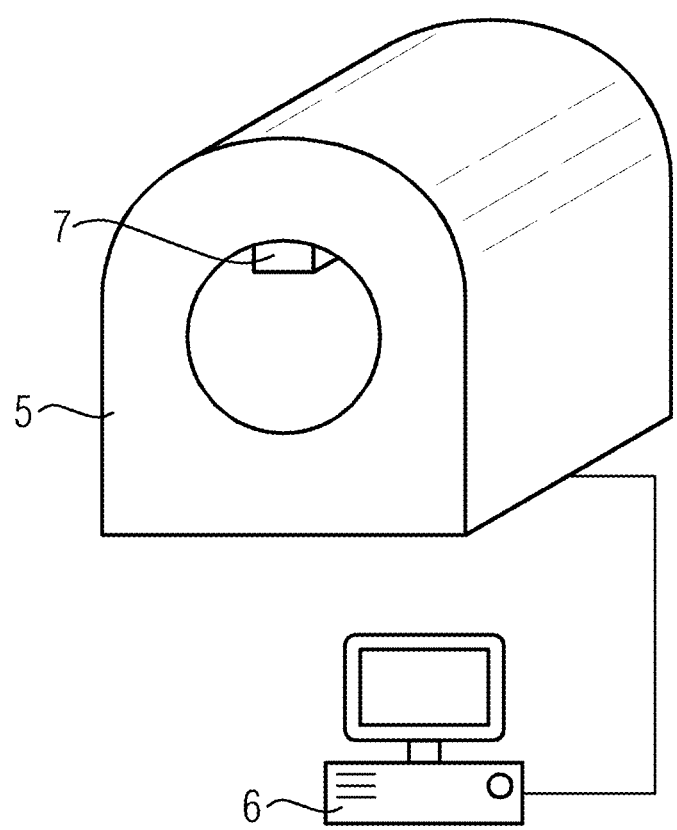
FIG. 4 depicts a schematic representation of an implementation of a system according to an embodiment.

In FIG. 4, a system for MRI according to an embodiment is depicted schematically.

The system includes an MRI scanner 5 coupled to a processing unit 6 or processor 6, that is configured to control the MRI scanner 5. The system further includes a camera system 7, that may also be controlled by the processing unit 6 or processor 6.

The processing unit 6 or a computer system including the processing unit 6 may also include a computer-readable storage medium with a computer program stored on it.

A system as shown in FIG. 4 may for example be used for performing a method according to an embodiment, for example as described with respect to FIG. 1 and FIG. 3.

According to an embodiment, motion artifacts in MRI images, for example for cases where several repetitions of MRI measurements are averaged, may be greatly reduced. This is for example achieved by combining a camera-based motion compensation and a tool-based registration. For synthetic contrast images using MDME approaches, an embodiment may be beneficial.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for magnetic resonance imaging (MRI) of an object, the method comprising:
   obtaining MRI data of the object during a first acquisition step and during a second acquisition step, wherein each acquisition step comprises at least two data acquisition periods;
   monitoring, by a camera system, a movement of the object during the first acquisition step and the second acquisition step;
   adjusting the MRI data obtained during the at least two data acquisition periods based on the monitoring;
   comparing, by a processor, MRI data obtained during a first reference period of the at least two data acquisition periods of the first acquisition step to MRI data obtained during a second reference period of the at least two data acquisition periods of the second acquisition step;
   correcting, by the processor, for each of the at least two data acquisition periods of the second acquisition step, the obtained or adjusted MRI data based on a result of the comparison; and
   generating, by the processor, a magnetic resonance image of the object based on the corrected MRI data.

2. The method of claim 1, wherein adjusting comprises:
   adjusting respective data sets of each of the data acquisition periods of the first and the second acquisition step depending on a result of the monitoring.

3. The method of claim 2, wherein each of the respective data sets is adjusted depending on the result of the monitoring at least once during the respective data acquisition period.

4. The method of claim 1, wherein adjusting comprises:
   comparing images acquired by the camera system during different data acquisition periods of the first acquisition step to each other; and
   adjusting the MRI data obtained during the data acquisition periods depending on a result of the comparison of the images.

5. The method of claim 1, monitoring comprises monitoring, by the camera system, a movement of one or more markers attached to the object.

6. The method of claim 5, wherein the camera system comprises at least two cameras having different positions with respect to at least one of the one or more markers.

7. The method of claim 1 wherein adjusting comprises:
   comparing at least one image taken by the camera system during the first reference period to at least one image taken by the camera system during a further data acquisition period of the second acquisition step; and
   adjusting the MRI data obtained during the data acquisition periods depending on a result of the comparison of the images.

8. The method of claim 1 further comprising:
   establishing a mapping rule depending on the result of the comparison of the MRI data obtained during the first reference period to the MRI data obtained during the second reference period; and
   correcting for each of the at least two data acquisition periods of the second acquisition step, the obtained or adjusted MRI data based on the mapping rule.

9. The method of claim 8, wherein the mapping rule corresponds to a Euclidian transformation.

10. The method of claim 1, wherein the MRI data obtained during the data acquisition periods of the first and the second acquisition step correspond to a layer of the object; and between two successive data acquisition periods of the first or the second acquisition step, MRI data for a further layer of the object are obtained.

11. The method of claim 1, further comprising:
    applying an excitation pulse to the object prior to or at a beginning of each of the data acquisition periods of the first or the second acquisition step.

12. The method of claim 11, wherein exactly one excitation pulse is applied to the object for two or more subsequent data acquisition periods of the first or the second acquisition step.

13. A system for magnetic resonance imaging (MRI) of an object, the system comprising:
    an MRI-scanner;
    a camera system; and
    a processor configured to:
      control the MRI-scanner to obtain MRI data during a plurality of acquisition steps including at least a first and a second acquisition step, wherein each acquisition step of the plurality of acquisition steps comprises at least two data acquisition periods;
      control the camera system to monitor a movement of the object during at least the first and the second acquisition step;
      adjust MRI data obtained during the data acquisition periods based on the monitoring;
      compare MRI data obtained during a first reference period of the at least two data acquisition periods of the first acquisition step to MRI data obtained during a second reference period of the at least two data acquisition periods of the second acquisition step;
      correct, for each of the at least two data acquisition periods of the second acquisition step, the obtained or adjusted MRI data based on a result of the comparison; and
      generate a magnetic resonance image of the object based on the corrected MRI data.

14. A non-transitory computer implemented storage medium that stores machine-readable instructions executable by at least one processor, the machine-readable instructions comprising:
    obtaining first MRI data of an object during a first acquisition step and second MRI data during a second acquisition step, wherein each acquisition step comprises at least two data acquisition periods;
    monitoring a movement of the object during the first acquisition step and the second acquisition step;
    adjusting MRI data obtained during the data acquisition based on the monitoring;
    comparing MRI data obtained during a first reference period of the at least two data acquisition periods of the first acquisition step to MRI data obtained during a second reference period of the at least two data acquisition periods of the second acquisition step;
    correcting for each of the at least two data acquisition periods of the second acquisition step, the obtained or adjusted MRI data based on a result of the comparison; and generating a magnetic resonance image of the object based on the corrected MRI data.

15. The non-transitory computer implemented storage medium of claim 14, wherein adjusting comprises:
adjusting respective data sets of each of the data acquisition periods of the first and the second acquisition step depending on a result of the monitoring.

16. The non-transitory computer implemented storage medium of claim 15, wherein each of the respective data sets is adjusted depending on the result of the monitoring at least once during the respective data acquisition period.

17. The non-transitory computer implemented storage medium of claim 14, wherein adjusting comprises:
comparing images during different data acquisition periods of the first acquisition step to each other; and
adjusting the MRI data obtained during the data acquisition periods depending on a result of the comparison of the images.

18. The non-transitory computer implemented storage medium of claim 14, wherein adjusting comprises:
comparing at least one image taken during the first reference period to at least one image taken during a further data acquisition period of the second acquisition step; and
adjusting the MRI data obtained during the data acquisition periods depending on a result of the comparison of the images.

19. The non-transitory computer implemented storage medium of claim 14, wherein the MRI data obtained during the data acquisition periods of the first and the second acquisition step correspond to a layer of the object; and between two successive data acquisition periods of the first or the second acquisition step, MRI data for a further layer of the object are obtained.

20. The non-transitory computer implemented storage medium of claim 14, wherein the machine-readable instructions further comprise:
applying an excitation pulse to the object prior to or at a beginning of each of the data acquisition periods of the first or the second acquisition step.

* * * * *